United States Patent
David et al.

(10) Patent No.: US 7,889,838 B2
(45) Date of Patent: Feb. 15, 2011

(54) INTERFEROMETER FOR QUANTITATIVE PHASE CONTRAST IMAGING AND TOMOGRAPHY WITH AN INCOHERENT POLYCHROMATIC X-RAY SOURCE

(75) Inventors: Christian David, Lauchringen (DE); Franz Pfeiffer, Brugg (CH); Timm Weitkamp, Ueberlingen (DE)

(73) Assignee: Paul Scherrer Institut, illigen PSI (CH)

( * ) Notice: Subject to any disclaimer, the term of this patent is extended or adjusted under 35 U.S.C. 154(b) by 0 days.

(21) Appl. No.: 11/921,709

(22) PCT Filed: May 30, 2006

(86) PCT No.: PCT/EP2006/005119
§ 371 (c)(1),
(2), (4) Date: Dec. 24, 2008

(87) PCT Pub. No.: WO2006/131235
PCT Pub. Date: Dec. 14, 2006

(65) Prior Publication Data
US 2009/0092227 A1 Apr. 9, 2009

(30) Foreign Application Priority Data
Jun. 6, 2005 (EP) .................................. 05012121

(51) Int. Cl.
*G03H 5/00* (2006.01)
(52) U.S. Cl. ........................................................ 378/36

(58) Field of Classification Search .................... 378/36, 378/70, 71, 84, 85, 98.8, 119
See application file for complete search history.

(56) References Cited

U.S. PATENT DOCUMENTS

| 5,812,629 | A | 9/1998 | Clauser | |
|---|---|---|---|---|
| 7,180,979 | B2 * | 2/2007 | Momose | ................... 378/62 |

FOREIGN PATENT DOCUMENTS

| EP | 1 623 671 A | 2/2006 |
|---|---|---|
| WO | WO 2004/058070 A | 7/2004 |
| WO | WO 2004/071298 A | 8/2004 |

OTHER PUBLICATIONS

Momose et al.: "X-ray talbot interferometry for medical phase imaging"; Jan. 13-14, 2004, Shiga (Japan); No. 716; pp. 156-159; XP002351238.
Momose et al.: "Demonstration of x-ray Talbot Interferometry"; Jul. 15, 2003, Tokyo (Japan); No. 42, Part 2; pp. 866-868; XP002976586; ISSN 0021-4922.

(Continued)

*Primary Examiner*—Courtney Thomas
(74) *Attorney, Agent, or Firm*—Laurence A. Greenberg; Werner H. Stemer; Ralph E. Locher

(57) ABSTRACT

An interferometer for X-rays, in particular hard X-rays, for obtaining quantitative phase contrast images, includes a standard polychromatic X-ray source, a diffractive optical beam splitter other than a Bragg crystal in transmission geometry, and a position-sensitive detector with spatially modulated detection sensitivity.

23 Claims, 7 Drawing Sheets

OTHER PUBLICATIONS

Weitkamp et al.: "X-ray Wavefront Analysis and Optics Characterization with a Grating Interferometer"; Jan. 24, 2005, USA; vol. 86, No. 5; XP002351239.

Weitkamp et al.: "X-ray phase imaging with a Grating Interferometer"; Aug. 8, 2005, USA; vol. 13, No. 16; pp. 6296-6304; XP002397629, ISSN 1094-4087.

Weitkamp et al.: "Hard x-ray Phase Imaging and Tomography With a Grating Interferometer"; Oct. 2004, Denver (USA); vol. 5535, No. 1; pp. 137-142; XP002397630.

Momose, A., "Medical Application of the X-ray phase contrast method"; UTLNL-R, Jul. 24, 2004, pp. 55-59—English abstract.

* cited by examiner

INTERFEROMETER FOR QUANTITATIVE PHASE CONTRAST IMAGING AND TOMOGRAPHY WITH AN INCOHERENT POLYCHROMATIC X-RAY SOURCE

CROSS-REFERENCE TO RELATED APPLICATIONS

The present application is a national stage application of International Application No. PCT/EP2006/005119, filed on May 30, 2006, which claims priority to European Patent Application No. 05012121.9, filed on Jun. 6, 2005, both of which are incorporated herein by reference.

BACKGROUND OF THE INVENTION

The present invention relates to an interferometer for X-rays, in particular hard X-rays, for obtaining quantitative phase contrast images and measuring wavefront shapes.

For hard X-rays, the cross section for absorption, which generates the contrast in conventional radiography, is usually much smaller than that for elastic scattering. The elastic scattering causes a phase shift of the wave passing through matter. If, for example, 17.5-keV x-rays (which are commonly applied for mammography) pass through a 50-μm-thick sheet of biological tissue, the attenuation will only be a fraction of a percent, while the phase shift is close to $\pi$. Thus, the possibility to record the phase shift of x-rays opens the potential for greatly enhanced contrast and, in consequence, reduction of the applied x-ray dose. Reduction of the dose is desirable i) because of health risks for patients exposed to x-rays, and ii) because of the reduced exposure times.

Several methods to detect phase variations in the radiation behind the sample were developed in the past years. They can be classified into interferometric methods, techniques using an analyzer crystal, and free-space propagation methods. These methods differ in the nature of the signal recorded, the experimental setup, and the requirements on the illuminating radiation (especially its spatial coherence and monochromaticity). Although some of them yield excellent results for specific problems, none is very widely used. In particular, none of them has so far found medical diagnostics applications, which require a large field of view of many centimeters, the efficient use of broadband radiation as provided by laboratory x-ray generators and a reasonably compact setup. In addition to medical applications, any investigation of low contrast objects, e.g., in biology or materials science could benefit from exploiting phase contrast. It should be mentioned that an object embedded in a matrix of the same absorption coefficient is completely invisible in absorption contrast, while for the same sample significant differences in phase shift may occur.

The use of gratings as optical elements in hard X-ray phase imaging has the potential of overcoming the problems that so far impair the wider use of phase contrast in X-ray radiography and tomography. Several different geometries of grating-based interferometers for hard x-rays have been investigated recently. The following contains a list of topics and results that have already been published, patented or made available in the past:

The international patent application WO 2004/071298 A1 describes the use of three gratings (two phase gratings and one amplitude grating) to obtain phase contrast images using a polychromatic, incoherent x-ray source. Further publications contain a description of results obtained with a grating based interferometer using two phase gratings and a Bragg analyzer crystal, or a phase grating together with an amplitude grating.

The experimental results known in the prior art were obtained at synchrotron x-ray sources, which are highly expensive installations and are only available at distinct scientific facilities.

At optical or x-ray wavelengths, the phase of a wave cannot be measured directly, so any conversion of a phase shift into an intensity modulation has to depend on interference of two (or more) waves. In order to be able to interfere constructively or destructively, the waves need to have a well-defined phase relation in time and space, i.e. sufficient temporal (longitudinal) coherence and spatial (transverse) coherence.

The commercial impact of an invention in context with radiography will greatly depend on whether an x-ray tube is suitable as radiation source or whether the method is restricted to use at synchrotron radiation facilities because of the required degree of coherence. Thus, a thorough understanding of the relevant terms and relations is essential to appreciate the advantages of the interferometer set-up according to the present invention.

Temporal coherence is related to the monochromaticity of the radiation. For radiation of a bandwidth of $\delta\lambda$ around a central wavelength $\lambda$, the longitudinal coherence length is $\lambda^2/\delta\lambda$. When considering two beams originating from the same source point that are superimposed after taking different paths through an optical set-up, these beams only have a well-defined phase relation if the difference in optical path lengths is shorter than the longitudinal coherence length. While for visible laser light $\lambda^2/\delta\lambda$ can extend over many meters, it is only in the order of a micron at hard x-ray wavelengths even when a crystal monochromator ($\lambda/\delta\lambda \approx 10^4$) is used.

Spatial coherence is related to the size and distance of the source. When considering an intrinsically incoherent and chaotic source (e.g. a light bulb or a conventional x-ray tube) of transverse size c emitting at a wavelength $\lambda$, then, at a distance l from the source, the wave-front phase difference between two points lying in a plane normal to the optical axis and separated by a distance r is well defined only if the condition $r < \lambda \cdot l/c$ is fulfilled. $t = \lambda \cdot l/c$ is called the transverse coherence length. Most importantly, interference effects such as those used in the grating-based interferometers can only occur when the coherence length is approximately equal to or larger than the relevant length scale of the diffraction aperture or phase mask. For an x-ray tube source with a spot size of 0.1 mm emitting at $\lambda=0.1$ nm, the transverse coherence length at a distance of 1 m from the source is again in the order of only one micron.

SUMMARY OF THE INVENTION

It is the object of the present invention to provide an apparatus for phase contrast x-ray images which does not rely on synchroton x-ray sources and which requires only little effort in adjusting the optical arrangements.

This objective is achieved in the present invention by an interferometer for X-rays, in particular hard X-rays, for obtaining quantitative phase contrast images, comprising:

a) an X-ray source, preferably a standard polychromatic X-ray source, b) a diffractive optical element, preferably in transmission geometry, that acts as a beam splitter, and c) a position-sensitive detector with spatially modulated detection sensitivity. This modulation acts as an analyzer for the interference pattern formed by the beam splitter; it can be integrated in the detector or separate from it.

This interferometer unifies all the requested requirements in using only a conventional X-ray source instead of a synchrotron source and in using only two different grating structures, one for diffracting the x-rays having passed through the object to be investigated, and the other one for delivering the spatially modulated detection sensitivity.

In a preferred embodiment of the present invention the beam splitter is a phase grating, that is, a line grating or a two-dimensionally structured grating with low X-ray absorption, but considerable X-ray phase shift, preferably with a phase shift of n or odd multiples thereof. The phase grating may be made by deep etching into silicon or a polymer.

Further, the modulation of the detector sensitivity can be achieved by a one- or two-dimensional grating structure with high X-ray absorption contrast, placed immediately in front of the detector. This analyzer grating may serve as an anti-scatter grid, or an anti-scatter grid can be used as the analyzer grating. The absorption grating can be made by deposition of a heavy metal into the gaps of a low-absorbing structure.

The periodicity $p_2$ of the detector sensitivity modulation is best chosen in such way that it is related to the period $p_1$ of the beam-splitter grating and to the radius l of the incident wavefront by the relation $$p_2 = \frac{1}{2} p_1 \cdot \frac{(d+l)}{l},$$

where d is the distance between the beam splitter and analyzer. Preferably, the distance between beam splitter and analyzer is chosen to be an odd fractional Talbot distance, given by the equation $$d_{n,sph.} = \frac{l \cdot d_n}{l \cdot d_n} = \frac{l \cdot n \cdot p_1^2 / (8\lambda)}{l - n \cdot p_1^2 / (8\lambda)},$$

wherein n=1, 3, 5, . . . .

Furthermore, the phase shift of the beam-splitter grating and the distance between beam splitter and analyzer can be adapted to a photon energy corresponding to an emission line of the X-ray generator used as the source.

In order to be able to observe moiré fringes of any desired period, or to minimize or altogether suppress moiré fringes, a mechanism can be included to vary the angular orientation around the optical axis of the beam splitter with respect to the analyzer.

For the purpose of increasing the lateral spatial resolution and to separate the information on X-ray phase shift from that of X-ray absorption, a one- or two-dimensional phase stepping scan can be implemented by lateral transverse movement of the radiation source and/or an aperture located in front of the radiation source, and/or of the beam splitter, and/or of the analyzer, and/or by a tilt of the interferometer with respect to the X-ray source.

To ensure fast data acquisition, the detector can be designed as being position-sensitive in two dimensions, whereby the lateral dimensions of the beam splitter and the analyzer cover a significant portion of the active area of the detector.

Alternatively, to keep production costs down and alleviate scattering artifacts in the interferograms, a collimator can be placed between the source and the beam splitter that limits the spatial extent of the illuminating X rays to a fan beam; a line-array detector and a mechanism can be comprised that allows a linear scan of the sample relative to the rest of the apparatus, perpendicular to the opening angle of the fan.

In both of the configurations named in the two previous paragraphs, the flux can be increased and data acquisition time thus reduced, by using, instead of a single line or spot source, a one- or two-dimensional array of individual physical or virtual sources that may be mutually incoherent and whose lateral separation $p_0$ is preferably given by $$p_0 = p_2 \times \frac{l}{d^*}.$$

This array of sources may be generated by an aperture mask with line- or dot-shaped openings. Alternately, the array of sources is generated by electron optics that creates an array of electron line or dot foci on the anode of the X-ray source. This can be achieved i.e. by generating the array of sources using electron optics that either scans a single line or dot focus across the anode surface of the X-ray source or projects an array of lines or dots onto the anode surface. Alternately or additionally, the array of sources can be generated by using an X-ray source comprising an anode which is structured either topographically or has assembled in a mosaic manner from different materials.

Again in order to improve the scanning properties of the interferometer, means for rotating the sample relatively to the remaining components can be comprised in order to perform data collection for a tomography scan.

In a preferred embodiment the scanning techniques can be carried out by implementing an analysis procedure for phase-stepping scan data that comprises the steps of calculating for each element of the detector the Fourier transform or at least one Fourier component of the intensity curve measured in the element, and then retaining the phase of one or more Fourier components as a signal for further processing.

Alternately, an analysis procedure can be implemented for phase-stepping scan data that comprises the steps of fitting for each element of the detector the intensity curve measured in the element to an intensity curve modeled or measured separately without the beam distortions under study, where at least one of the fit parameters is the shift of the curve along the position axis of the scan.

Additional advantageous features of the present invention can be derived from the remaining depending claims.

BRIEF DESCRIPTION OF THE SEVERAL VIEWS OF THE DRAWINGS

Preferred examples and embodiments of the present invention are described hereinafter with reference to the accompanying drawings, which depict in.

DETAILED DESCRIPTION OF THE INVENTION

Figure 1:
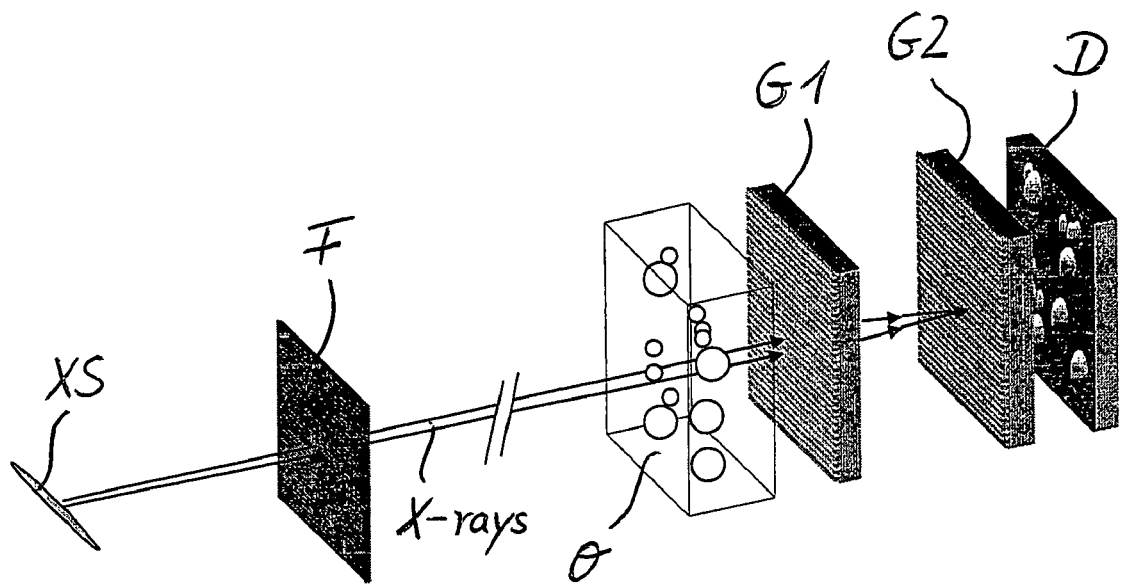
FIG. 1 a schematical view on a two-grating interferometer according to the present invention.
Figure 1:
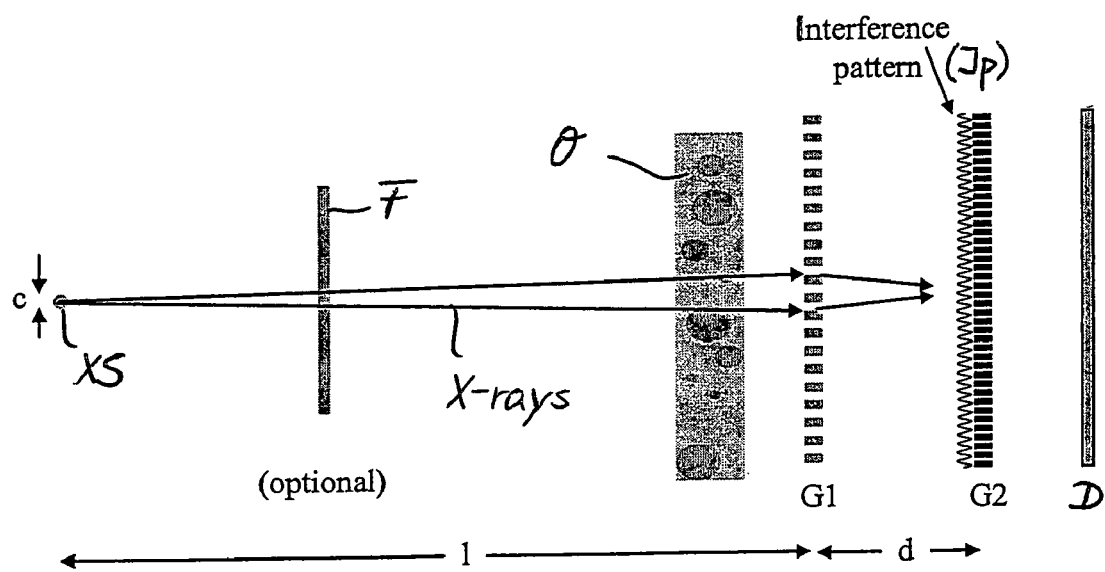

The basis of the present invention is the two-grating interferometer as it is shown in FIG. 1. It comprises the following components: an x-ray source XS (e.g. a stationary or rotating anode with a typical electron energy in the range of 10 to 100 keV, or any other X-ray source), an optional set of appropriate filters F, an object O, a beam splitter phase grating G1, an analyzer amplitude grating G2, and a spatially resolving x-ray detector D. The source XS provides some degree of spatial coherence at least in one direction perpendicular to the optical axis A. If the source is an X-ray tube, then the anode material should be chosen to have appropriate lines in the energy range well suited for the specific application. For mammography these could be Nb, Mo, Rh, Pd, Ag, which have K-emission lines in the 15 to 25-keV region. For other applications with thinner or less absorbing samples (e.g. desktop tomography setups) the energy would be in the range of 5-10 keV (e.g. a Cu anode). The spectrum of the source XS may be filtered to reduce the source bandwidth. The coherence requirements are defined in more detail further below.

Regarding the image formation process the beam splitter grating G1 with a period $p_1$ should be constructed such that it divides the incoming beam essentially into the two first diffraction orders. The conditions for this are that the grating lines have little absorption and shift the phase of the radiation passing through the grating lines by an odd multiple of $\pi$, and that the width of the phase-shifting structures is close to half of the grating period, i.e., that the grating has a duty cycle close to 0.5. Since the wavelength of the illuminating hard x-rays is on the order of $10^{-10} \ldots 10^{-11}$ m, and thus much smaller than the grating pitch ($10^{-5} \ldots 10^{-6}$ m), the angle between the two diffracted beams is so small that they overlap almost completely. In the overlap region downstream of the beam splitter grating G1, the diffracted beams interfere and form linear periodic fringe patterns in planes perpendicular to the optical axis A at a distance d down-stream of G1. For a spherical incident wave, i.e. for radiation coming from a source at a distance l the period of the interference pattern is equal to $$p_2 = \frac{1}{2} p_1 \cdot \frac{(d+l)}{l} \quad (1)$$

If d<<1, which is usually the case, the period of the interference fringes is about half of the period of G1. Neither the period nor the lateral position of these fringes depends on the wavelength of the radiation used. Perturbations of the incident wave front, such as those induced by refraction on a phase object in the beam, lead to local displacement of the fringes. A fundamental idea for the operation of the grating-based interferometer described here is to detect the positions of the fringes and determine from these the shape of the wave front. However, since the periodicity of the phase grating (and thus the spacing of the interference fringes) does not exceed a few microns, an area detector placed in the detection plane will generally not have sufficient resolution to resolve the fringes, let alone the exact position of their maxima. Therefore, an analyzer grating G2 with absorbing lines and the same periodicity $p_2$ and orientation as the fringes is placed in the detection plane, immediately before the detector. The transmission of the absorber lines should be as low as possible, and the width of the absorber lines should be close to the width of the gaps in between them (duty cycle close to 0.5) to give optimum performance. This analyzer grating G2 acts as a transmission mask for the detector D and transforms local fringe position into signal intensity variation. The detected intensity signal contains quantitative information about the phase shift induced by the object O. At least three methods can be applied to extract this phase information:

1) Simplest method—When the analyzer grating G2 is placed into the interference fringe pattern of the empty set-up (meaning the case without sample) with exactly the same orientation and periodicity of the grating lines and the interference fringes, then the transmission of the transmitted intensity depends on the relative position of fringes and grating lines in the direction perpendicular to the grating lines. In the case when the maxima of the interference fringes coincide with the absorbing grating lines, the transmitted intensity reaches a minimum whereas it will reach a maximum when the maxima of the interference fringes coincide with the transmitting gaps between the absorbing lines. If this position is chosen such that the transmitted intensity is between these extreme values, and ideally close to the average between the maximum and minimum transmission, then a local distortion of the interference fringes will cause a change in the local transmission proportional to fringe distortion. A phase object introduced upstream of the gratings will cause a distortion of the transmitted wave front that in turn will cause a distortion of the interference fringe pattern. It can be shown, that this distortion is proportional to the derivative of the phase shift induced by the object O. The recorded image is therefore a differential phase contrast image. If required, a phase contrast image can be obtained by integration of the differential phase contrast image in the direction perpendicular to the grating lines. The disadvantages of the methods mentioned above are the following: i) the recorded image contains possible absorption contrast and contrast from diffraction of edges inside the object O. Both are difficult to distinguish from the (differential) phase contrast contribution. ii) The method requires an exact alignment of the interference pattern with respect to the analyzer grating lines over the whole field of view. This may be difficult to obtain especially for large fields of view, and even impossible when either the interference fringes or the grating lines are distorted due to mechanical imperfections of the set-up or fabrication errors of the gratings.

Figure 2:
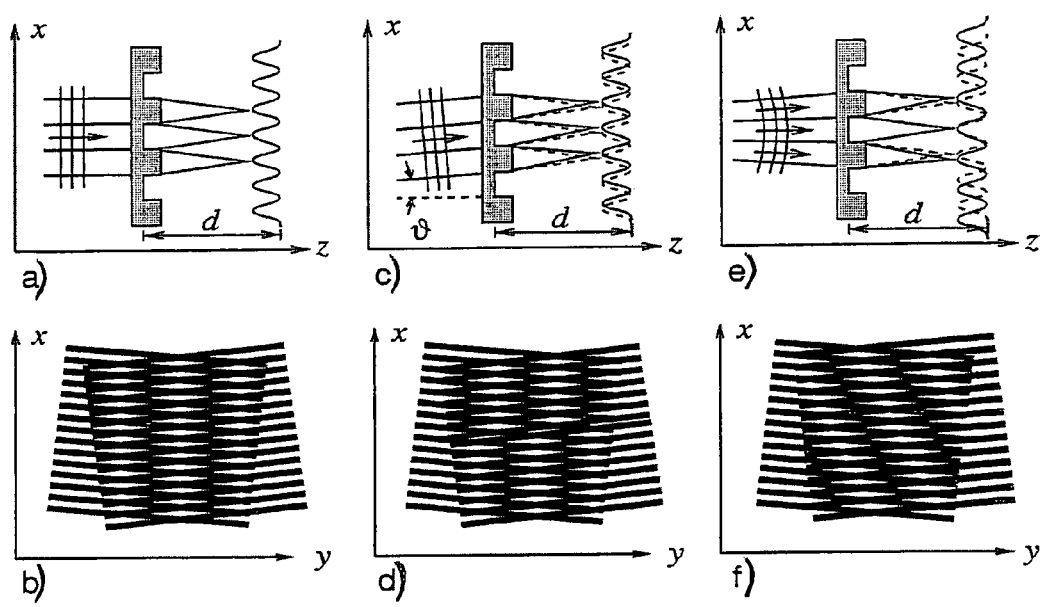
FIG. 2 a schematical view on Talbot self-imaging of a linear phase grating and moiré fringe formation using the interferometer according to FIG. 1.

2) Moiré interferometry—In this mode, the beam-splitter grating G1 and the analyzer grating G2 are not aligned with their lines perfectly parallel to each others', but rather with a deliberate, small rotation angle α of the two gratings with respect to one another, about the optical axis. This results in a set of moiré fringes as shown in FIG. 2. For an incident plane wave (FIG. 2a), the moiré fringes have a spacing $$p_m = p_2/\alpha \quad (2)$$

and are perpendicular to the lines of the two gratings (FIG. 2b). For an inclined wave that is still plane, the fringes are displaced with respect to the plane wave parallel to the optical axis (FIGS. 2c, d). For a converging or diverging (FIG. 2e) wave, the moiré fringes are inclined (FIG. 2f). From the local positions of the moiré-fringe maxima or from the local moiré-fringe inclination, the derivative of the wave-front phase profile can be obtained relatively simply. The relationship between the lateral moiré-fringe displacement Δy and the wavefront phase Ø is $$\frac{\partial \Phi}{\partial x} = \alpha \frac{\Delta y}{d}. \quad (3)$$

Figure 3:
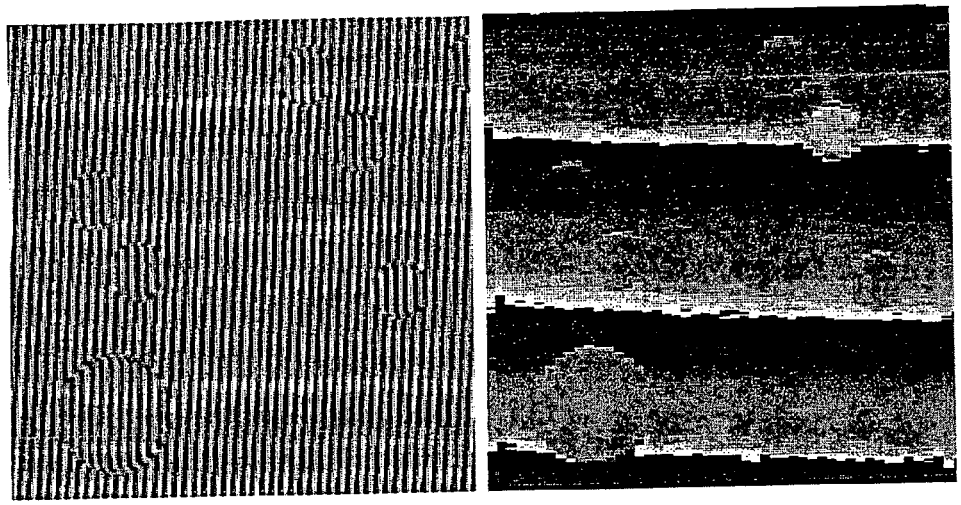
FIG. 3 a schematic view on Moiré interferometry.

Standard fringe-analysis methods and software can be used to obtain the moiré-fringe positions Δy. FIG. 3 shows an example of experimental data and a preliminary analysis. The choice of the inclination angle α of the two gratings is determined by a tradeoff between spatial resolution and sensitivity. The spatial resolution in the direction normal to the moiré fringes cannot be much better than one moiré-fringe period $p_m$. Since $p_m$ decreases with increasing α (Eq. 2), stronger tilt means better spatial resolution. But Eq. 3 shows that the sensitivity decreases with increasing tilt, i.e., for a given phase gradient the moiré fringes are less displaced for stronger α. The main advantage of moiré operation of the interferometer is that pure phase information, without any unwanted absorption contrast, can be obtained from a single image. The main disadvantage is that the resolution in the direction parallel to the grating lines (normal to the moiré fringes) is at least one order of magnitude poorer than the pixel size of the detector.

Figure 4:
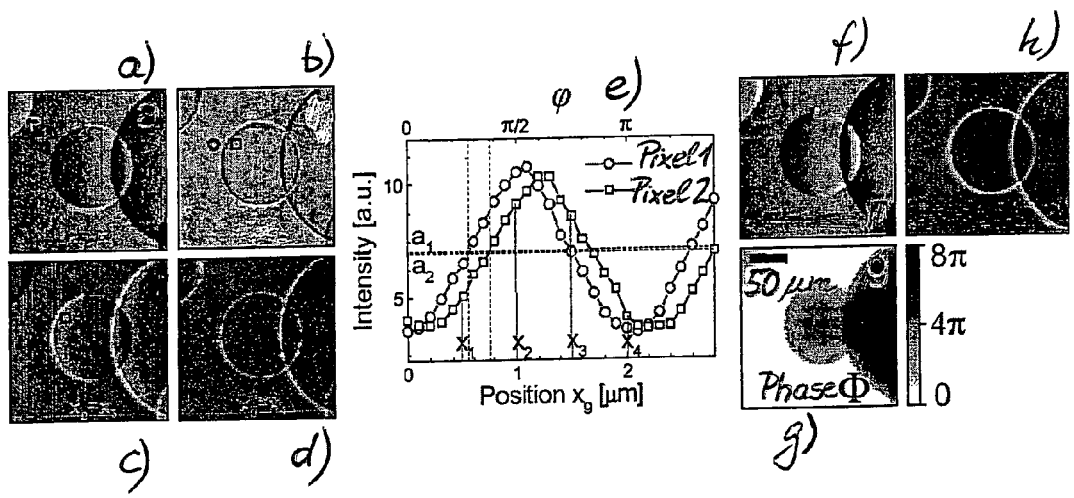
FIG. 4 a schematic view on the principles of the phase stepping technique used with the interferometer according to FIG. 1.

3) Phase stepping—A third method that avoids the disadvantages of the approaches described above is the following: to separate the phase information from other contributions to the signal, such as absorption in the sample, inhomogeneous illumination or imperfections of the gratings, the phase-stepping approach used in visible-light interferometry was adapted to this setup. It is illustrated in FIG. 4: one of the gratings is scanned along the transverse direction perpendicular to the grating lines over one period of the grating, and for every point of the scan an image is taken (FIGS. 4a to d). The intensity signal I(x, y) in each pixel (x, y) in the detector plane oscillates as a function of $x_g$ (FIG. 4e). The phases of the intensity oscillations in each pixel, φ(x, y) (FIG. 4f) are related to the wavefront phase profile Φ(x, y) by $$\varphi(x, y) = \frac{\lambda d}{p_2} \frac{\partial \Phi(x, y)}{\partial x}. \quad (4)$$

φ contains no other contributions, particularly no absorption contrast. The phase profile of the object can thus be retrieved from φ(x, y) by a simple one-dimensional integration, as shown in FIG. 4g. In the general case where the wavefront impinging on the object O already shows some distortion, the background phase distribution $\Phi_{back}(x, y)$. should be measured with the object O removed from the beam and then subtracted. Even in cases where the range of phase values exceeds 2π by far, such as in the example in FIG. 4g, phase unwrapping is generally not necessary because the measured quantity φ, essentially the first derivative of Φ (Eq. 4), will not exceed π as long as the phase gradients in the sample are not too steep.

Another quantity contained in the information obtained by a phase-stepping scan, the average signal for each pixel over an entire oscillation, a(x, y) (FIG. 4h), is identical to the transmission radiography signal as it would be measured in a radiograph taken without the interferometer. It contains the projected absorption coefficient and, depending on experimental geometry and detector resolution, edge-enhancing Fresnel diffraction contrast. A single phase-stepping scan thus yields both the phase and the absorption image. The full resolution of the detection system can be used in both images. The main disadvantage is the fact, that several images have to be acquired to obtain a phase image. This however does not necessarily mean, that the applied x-ray dose or exposure time has to be increased.

Figure 5:
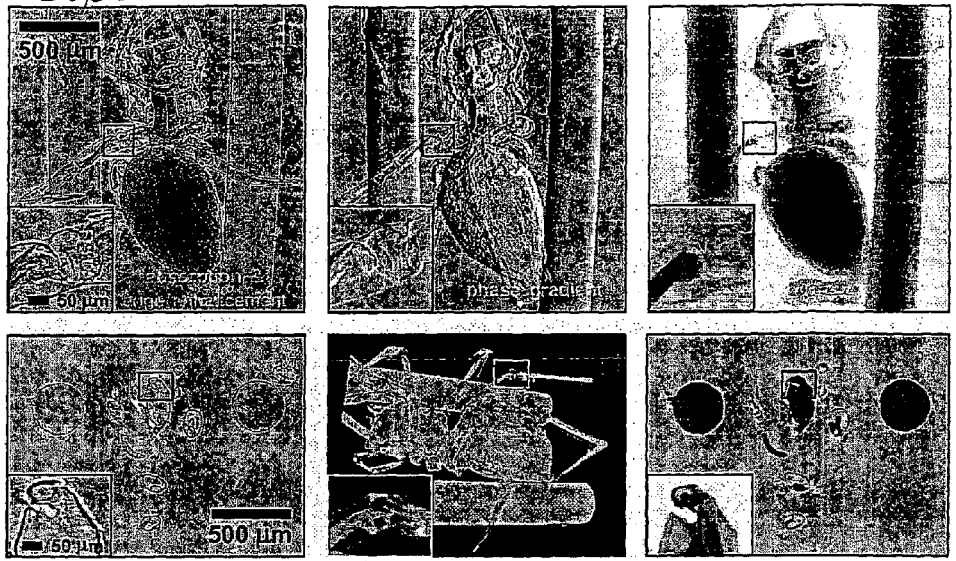
FIG. 5 tomography images obtained with phase stepping interferometry.

FIG. 5 shows processed radiographs a(x, y) and φ(x, y) obtained by phase stepping, the integrated phase shift Φ(x, y), as well as reconstructed tomograms of both the absorption and the phase signal and a three-dimensional rendering of the tomographically reconstructed refractive index of the sample, a small spider. The edge-enhanced absorption image a(x, y) shows strong contrast for fine details both in projection (FIG. 5a) and tomogram (FIG. 5d). But low spatial frequencies of the phase distribution are lost, so that image segmentation, i.e., the assignment of each pixel or voxel to one of the constituent materials of the sample, is not easily possible. The phase tomogram (FIG. 5f) exhibits a clear advantage: its pixel values are a direct measure of the decrement of refractive index δ in the sample, and are therefore directly accessible to quantitative analysis. Moreover the edge enhancing inline Fresnel diffraction contrast in FIGS. 5a and d would not be observable at lower resolutions of the detector whereas the interferometric phase contrast is not subject to such a limitation. This is of crucial importance when the interferometric method is scaled up to large fields of view, as the limited number of pixels will inherently limit the spatial resolution.

Figure 6:
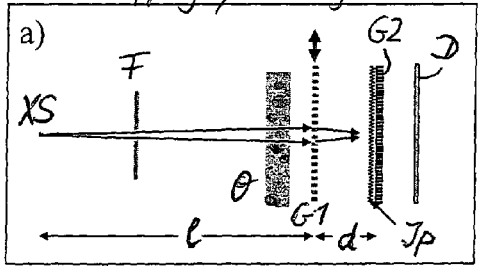
FIG. 6 a schematic view on four different options to obtain phase stepping movement for the two grating interferometer according to FIG. 1.
Figure 6:
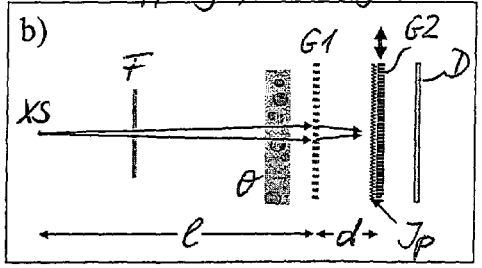

It should be mentioned that there are several possibilities to perform the phase stepping: the most obvious is to move either the grating G1 according to FIG. 6a or the grating G2 according to FIG. 6b. The disadvantage is that the movement has to be done with sub-micron accuracy and that the exact parallel orientation of the lines of both gratings may be lost, especially when large gratings are used to provide a large field of view. Instead it is also possible to rotate the grating G1 and the grating G2 together around an axis oriented along the direction of the grating lines by an angle α as indicated in FIG. 6c. This again allows to keep the gratings G1 and G2 in an aligned position with respect to each other or even to mechanically fix both gratings together. The most advantageous possibility is to move the source in the direction perpendicular to the optical axis and the grating lines as shown in FIG. 6d. This may be easier as the movement is coarser and has to be performed with l/d times less precision as compared to the first two solutions a and b. Again it allows to keep the gratings G1 and G2 in an aligned position and to mechanically fix them so that the alignment cannot be not lost during the phase stepping movement.

The source can be moved either mechanically or by deflecting the electron beam of the x-ray source to move the position of the electron impact on the anode. In case of the usual geometry of an x-ray tube where the x-rays are extracted under a shallow angle from the anode surface, the movement of the source point also has a larger component along the optical axis. Here only the component perpendicular to the optical axis has an effect on the phase stepping. The total deflection of the beam on the anode surface is in this case larger reducing the requirements on the accuracy of the electron beam movement.

As mentioned above and illustrated in FIG. 4, a phase-stepping scan yields, for each pixel in the detector, a series of intensity values from which different quantities can be extracted, especially the phase φ of the intensity oscillation in each pixel, which is related to the derivative of the wavefront phase Φ by eq. (2), and the average intensity a over an oscillation period, which essentially corresponds to the non-interferometric X-ray image. Hereinafter it is discussed how many phase steps need to be made in one phase-stepping scan, and how the phase-stepping scan is analyzed to extract φ.

The range of the phase stepping scan should cover (at least) one period of the oscillation. In conventional phase-stepping interferometry (i.e. with visible light), the optical components are usually designed such that the contrast curve (as shown, e.g., in FIG. 4e) is sinusoidal. In that case it is sufficient to take three points in a scan. The tangent of the phase φ of the oscillation is then easily calculated by just taking the ratio of signal differences.

The situation in the X-ray interferometer differs from the conventional one in that the shape of the contrast curve is not sinusoidal. (For the ideal case of box-profile gratings and fully coherent illumination, it would, for example, be triangular.) There are at least two ways to cope with this problem:
1. Perform phase-stepping scans with a larger number of points per oscillation period. To analyze the phase-stepping scan signal for each pixel, its Fourier transform can be calculated. The phase of the first component of the Fourier transform represents the oscillation phase φ (wrapped into a half-open interval of width π). The minimum number of points in the phase-stepping scan for this type of analysis should be the number of the highest Fourier component of non-negligible intensity, plus 2.
2. In a calibration measurement without any sample, measure the contrast curve (in each pixel) by taking a phase-stepping scan with very fine steps. In imaging of samples, phase-stepping scans can be performed with few points in the scan, and the phase φ determined by using the calibrated contrast curve, for example with a fitting procedure.

When comparing the two methods, it should be noted that the first method has the drawback of more necessary points per phase-stepping scan, but the advantage that higher Fourier components can potentially be used to extract additional information.

The distance d between the two gratings can be chosen freely, although there are values of d for which the contrast is best and others for which it has a minimum (see below). As can be seen from equation (2), the sensitivity of the method increases linearly with d. The choice of larger d may result in a loss of spatial resolution due to penumbral blurring, as the distance between the object and the detector is increased. Moreover a higher degree of lateral coherence is required (see below).

When choosing the inter-grating distance d, the contrast of the interference fringes changes periodically as a function of d. For a plane incoming wave and a pure phase grating of pitch $p_1$ whose lines shift the phase by π, the contrast is strongest for odd multiples of $d=p_1^2/(8\lambda)$ and vanishes for even multiples of $d=p_1^2/(8\lambda)$, —a phenomenon related to the Talbot self-imaging effect. In the following, one refers to any distance $d_n=n\, p_1^2/(8\lambda)$ as the "n-th fractional Talbot distance" and to the planes at a distance $d_n$ from the phase grating as the "n-th fractional Talbot plane". d should be set to values giving maximum contrast, i.e. to an odd fractional Talbot distance (n=1, 3, 5, . . . ). For a spherical incoming wave instead of a plane wave, the expression above for the fractional Talbot distances has to be modified to $$d_{n,sph.} = \frac{l \cdot d_n}{l - d_n} = \frac{l \cdot n \cdot p_1^2/(8\lambda)}{l - n \cdot p_1^2/(8\lambda)}. \quad (5)$$

where l denotes the distance between the source and G1. For l>>$d_n$, the difference between $d_n$ and $d_{n,\,sph.}$ is small.

As already mentioned, neither the period nor the lateral position of these fringes depends on the wavelength of the radiation used. In this sense the described setup is achromatic allowing for the use of broadband radiation from an x-ray tube without the need of monochromators that would only cut out a small fraction of the used radiation and would therefore not be photon efficient.

However, two aspects of the proposed set-up do depend on the photon energy. Firstly, the phase shift of the lines of the grating G1 depends on the photon energy due to the dispersion of the grating material. The condition to induce a phase shift equal to odd multiples of n is not strict, and a radiation within a certain energy band in the order of ±10% around the design energy can be accepted. A deviation from n only affects the contrast—but it does not change the interference pattern qualitatively. Secondly, the position of the Talbot planes depends on the photon energy. But again the condition that the grating G2 has to be placed in a Talbot plane is also not very strict, allowing the use of radiation within a certain energy band in the order of ±10% for the grating G2 placed in the first Talbot plane. This condition becomes stricter for higher grating distances.

It should be mentioned that also the refractive index of the object depends on the photon energy used. Nevertheless, reconstructed phase projections and tomograms will still be quantitative under the condition that the elements contained in the sample have no absorption edges in the range of the used photon energy band. In this case, all parts of the sample have the same dispersion relation, i.e. the real part of the refractive index changes with $E^{-2}$.

The considerations of the previous sections show that the phase shift induced by the structures of the grating G2 should be close to odd multiples of π and that the distance between the grating G1 and the grating G2 should be close to an odd fractional Talbot distance $d_{n,\,sph.}$. Both, phase shift and fractional Talbot distance, depend on the wavelength of the radiation used. It is therefore important that the grating structures and the distance chosen between the grating G1 and the grating G2 are matched to each other, meaning that both fulfill the conditions for the same wavelength. Moreover, it might be useful if this wavelength coincides with an emission line of the anode material of the used x-ray source. As mentioned above, the acceptable bandwidth is wide compared to other interferometric methods. In particular, it is wide enough to accept a series of emission lines (e.g. the Cu—K$_{<1}$, Cu—K$_{<2}$ and Cu—K®—lines emitting at 8.048, 8.028 and 8.905 keV photon energy, or the Mo—K$_{<1}$, Mo—K$_{<2}$ and Mo—K®—lines emitting at 17.479, 17.374 and 19.608 keV photon energy, or the Ag—K$_{<1}$, Ag—K$_{<2}$ and Ag—K®—lines emitting at 22.163, 21.990 and 24.942 keV photon energy).

The setup described requires spatial coherence only in the direction perpendicular to the optical axis A and to the grating lines. In this direction the minimum required coherence length t is $$t = 4d \cdot \frac{\lambda}{p_1}. \quad (6)$$

If the grating G2 is placed in the first fractional Talbot plane, then $t=p_1/2$. For grating periods in the range of several microns, t is therefore in the order of one micron. As described before, the size of a source emitting at wavelength $\lambda=0.1$ nm and placed at a distance $l=1$ m from the beam-splitter grating G1 should be smaller than 0.1 mm along the direction perpendicular to the grating lines. The use of a smaller source will increase the spatial coherence, resulting in an improvement of the phase contrast. As there are no limitations in terms of coherence in the direction along the grating lines, a line source can be used.

In medical x-ray imaging, where samples with thicknesses of many cm are viewed, scattering of x-rays in the sample generates diffuse background intensity on the detector that reduces the obtained contrast and image quality. Therefore, usually, an array of collimating absorbers, called an anti-scatter grid, is mounted in front of the detector to block radiation that has been deflected by a significant angle. This grid can be either a two-dimensional array of absorbing structures or a one-dimensional array. In the grating interferometer setup described here, the grating G2 comprises structures that are 5 to 10 microns thick—depending on the photon energy used—to provide sufficient x-ray absorption and that have, at the same time, widths on the order of one micron. The aspect ratio of the structures is therefore usually much greater than unity. The grating G2 can therefore also act as an anti-scatter grid. Likewise, in principle, the anti-scatter grid of an x-ray imaging system may be used as the analyzer in a grating based interferometer, although this would require that the period of the anti-scatter grid be smaller than is the case in commonly available systems.

Figure 7:
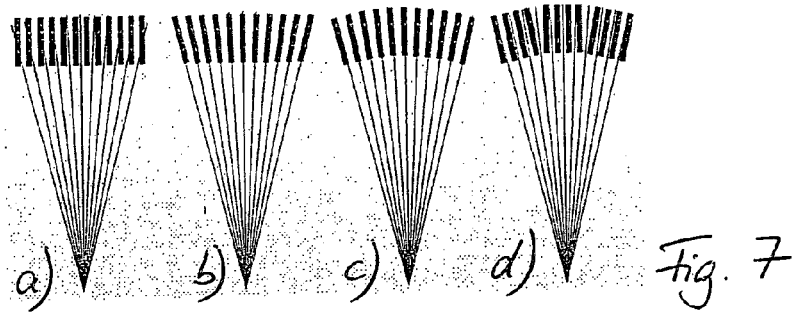
FIG. 7 a schematic view on the cone-beam problem and a number of solutions for it.

In many X-ray imaging applications that require a field of view of many centimeters (such as in medical diagnostics) the divergence angle of the x-ray beam is considerable, as the source cannot be placed at distances too far from the detector. Due to the high aspect ratio of the grating structures in the interferometer, especially of the grating G2, the beams in certain regions close to the edges of the field of view may pass through the gratings under too large angles. Only the angular component within the drawing of the lower part of FIG. 1 has an effect. To completely avoid this problem, the grating structures have to be bent or curved as depicted in FIGS. 7a to d, or a scanning scheme with appropriate orientation of the gratings has to be applied. To cope with this problem that the rays far from the center of the beam cone or fan will be obstructed by the lines of a flat deep grating as shown in FIG. 7a) different solutions can be applied. FIG. 7b) illustrated a solution by bending the grating lines on a flat substrate. FIG. 7c) schematically depicts the grating lines being placed on a curved surface. Finally, FIG. 7d) shows a way that segments of a flat grating approximating the curved or bent geometry.

Figure 8:
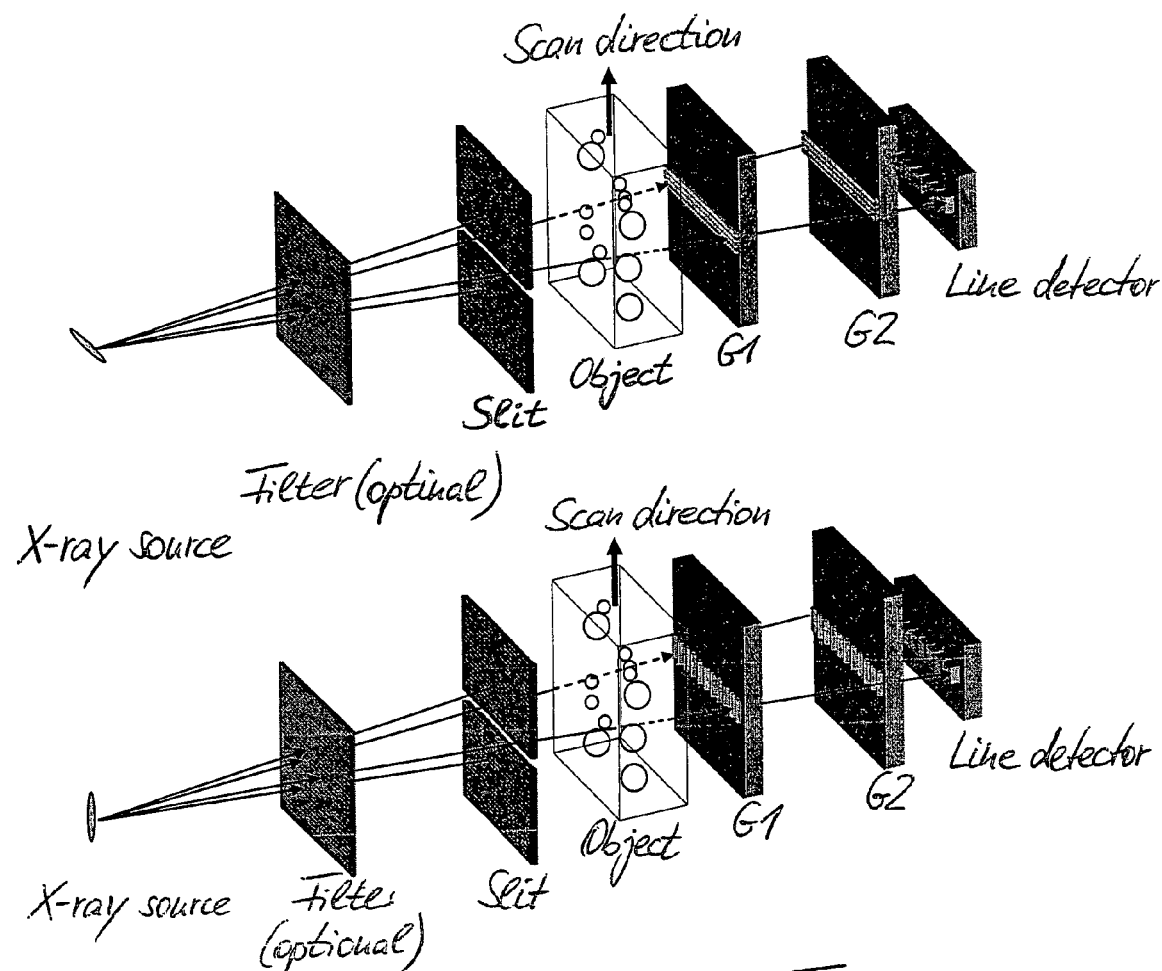
FIG. 8 a schematic view of a two grating interferometer implemented in a scanning x-ray imaging system, whereby two possible orientations of the grating lines with respect to the fan beam are shown.

Besides full-field radiography systems, in which a two-dimensional X-ray detector is used to obtain projection images of a sample, scanning systems are also applied in medical X-ray imaging. As illustrated in FIG. 8, a slit S placed between the source XS and the sample O generates a fan-shaped beam, and a one-dimensional line detector $D_1$ can be used, with its elements aligned to the fan. The two dimensional projection of the sample O is obtained by either scanning the sample through the fan-beam, or by scanning the beam across the sample and moving the line detector $D_1$ with the beam. The detector $D_1$ is read out at different positions during the scan and a two-dimensional image is created line by line.

Although the mechanical setup is more complicated, the scanning scheme has some important advantages compared to a two-dimensional setup: i) a suppression of diffuse scattering without an anti-scatter grid, since the slit S, together with the limited size of the source spot, acts as a collimator, ii) lower cost and higher detection efficiency of one-dimensional detectors in comparison with two-dimensional detectors. The grating based phase contrast can also be applied to a scanning scheme, as shown in FIG. 8. The advantage is that only gratings over a smaller area are required compared to a full-field imaging scheme, which will significantly reduce the cost. Two possible orientations of the grating lines with respect to the fan beam are shown, either with the grating structures along the slit direction (above) or with the grating lines perpendicular to the slit direction (below). The arrangement show in the upper part of FIG. 8 has the advantage that it avoids the cone beam problem (see previous section).

Figure 9:
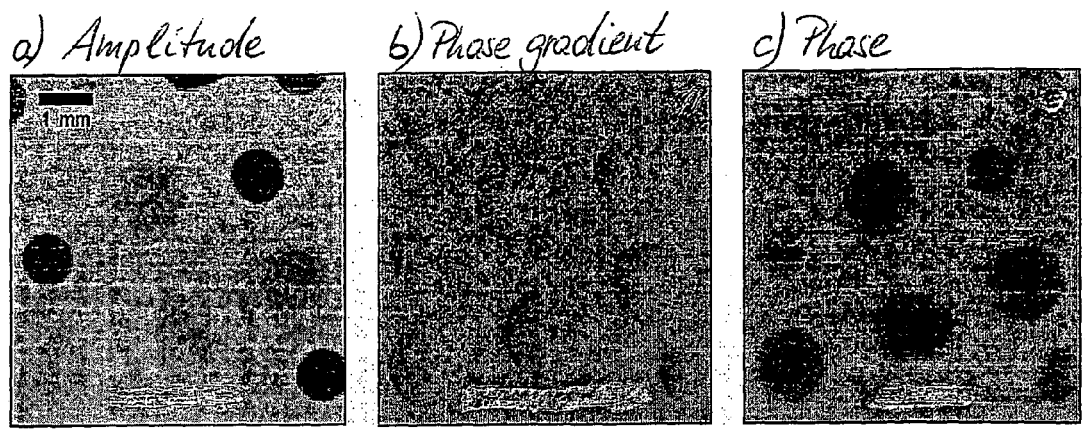
FIG. 9 x-ray images of a test sample containing aluminium and plastic spheres.

FIG. 9 shows x-ray images of a test sample containing poly-methylmethacrylate (PMMA, 1.5 mm diameter) and Aluminum (1.0 mm diameter) spheres. The images were recorded using a standard, sealed x-ray tube source with a Mo anode operated in line focus mode (8 mm×0.04 mm) at an electron energy of 40 keV and an anode current of 25 mA, placed at a distance $l=1.7$ m from the beam splitter phase grating G1. For the Mo—K<emission lines, the coherence length along the smaller source dimension (c=0.04 mm) is $t=\lambda \cdot l/c \supset 3$ μm at the position of G1. The two gratings G1 and G2 had periods of $p_1=3.94$ μm and $p_2=2.0$ μm. They were spaced by the first fractional Talbot distance, $d_1=28.4$ mm. Apart from the 500-μm-thick silicon substrates supporting the gratings, no additional filter was inserted in the x-ray beam. This means that the whole Mo K-emission series and large parts of the bremsstrahlung spectrum contributed to image formation. The detector was a fiber-coupled CCD (model "Hystar", manufacturer Photonic Science) with an effective pixel size of approximately 30 μm. The data were acquired by phase stepping with 17 steps over 1 oscillation period, with an exposure time of 50 s for each CCD frame.

In the conventional amplitude contrast image, the aluminum spheres are clearly visible (FIG. 9a). The absorption coefficient of the plastic spheres is about 20 times lower than that of Al. In the phase gradient and integrated-phase images (FIGS. 9b, c) the contrast for the plastic spheres is strongly increased.

Figure 10:
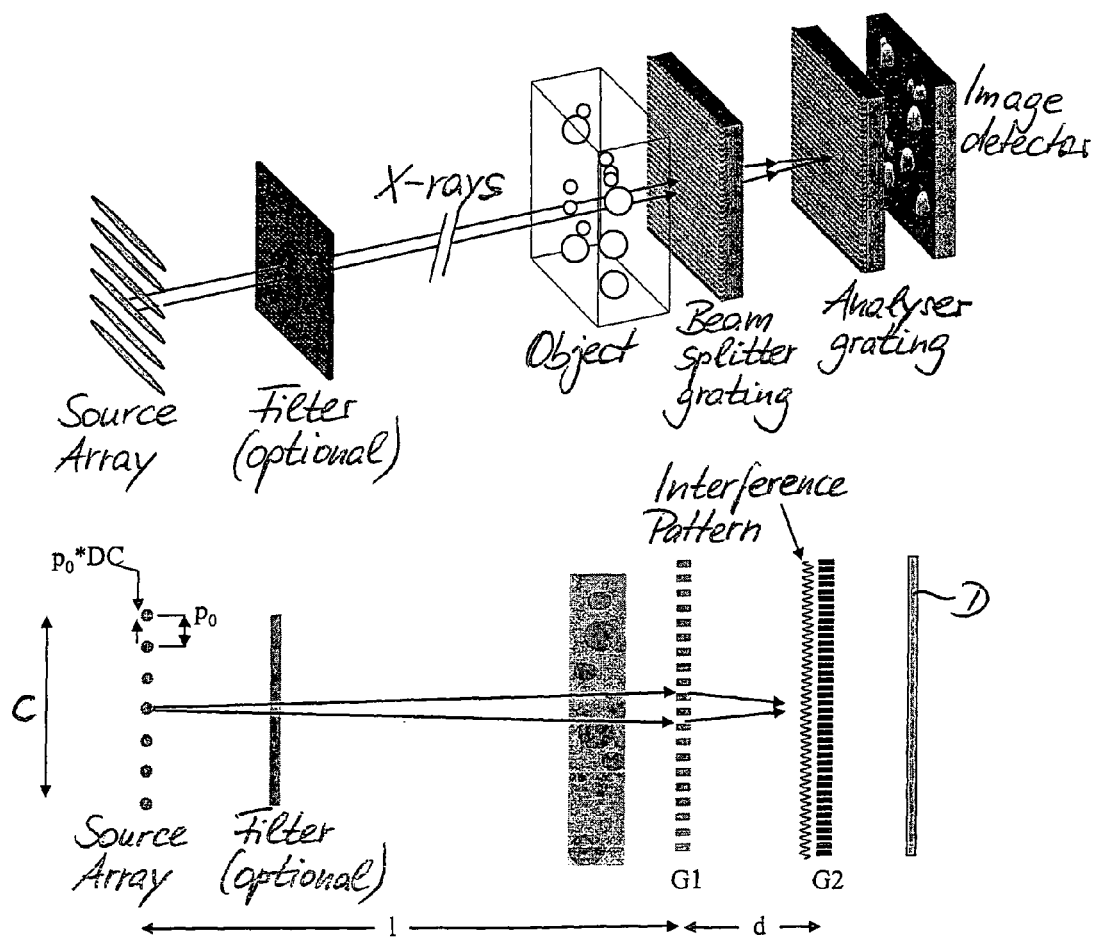
FIG. 10 a schematic view on a grating interferometer with an array of line sources.

Due to the requirements of spatial coherence described above, the choice of the source geometry is limited to relatively narrow line sources placed at large distances from the sample. This results in low x-ray flux density and thus in long exposure times. The following section describes a setup that can record phase contrast images with much higher flux density. The schematic setup of the proposed design is shown in FIG. 10. The difference to the previously described interferometer shown in FIG. 1 is the x-ray source that consists of an array of N line sources. The line sources are oriented along the grating lines and the width of each source line is chosen narrow enough to provide sufficient spatial coherence in the direction perpendicular to the grating lines. Thus, each of the line sources is intrinsically coherent, whereas the lines can be mutually incoherent. The spacing of neighboring source lines, i.e. the period $p_0$ of the source array is chosen such that the shift of the interference patterns created by two neighboring virtual line sources along the direction perpendicular to the grating lines is exactly $p_2$. This condition is fulfilled for:

$$p_0 = p_2 \times \frac{l}{d}. \quad (7)$$

The relationship between the periods $p_0$, $p_1$, and $p_2$ of the source array, the beam-splitter grating and the analyzer grating is $$p_1 = \frac{2 p_0 p_2}{p_0 + p_2}. \quad (8)$$

Another useful relationship is that for operation in the n-th fractional Talbot distance, the distance l between the source array and the beam-splitter grating is $$l = \frac{n}{2\lambda} \times \frac{p_0^2 p_2}{p_0 + p_2}, \quad (9)$$

which is particularly useful when solved for $p_0$:

$$p_0 = \frac{\lambda l}{n p_2} + \sqrt{\left(\frac{\lambda l}{n p_2}\right)^2 + \frac{2\lambda l}{n}}. \quad (10)$$

The arrangement also works for source array periods that are integer multiples of $p_0$. The size c of the source array can be much bigger than the width s of an individual line source. The duty cycle $DC=s/p_0$ of the source array determines the degree of transverse coherence in the direction perpendicular to the interferometer grating lines. The interference patterns of all N virtual line sources add up incoherently (as the virtual line sources are mutually incoherent) but preserving contrast.

Therefore, the flux density is increased by a factor N compared to a single line source. It is also useful to note that the setup results in a decoupling of the resolution limit due to penumbral blurring, $\delta_{pen}=c\,d/l$, from the coherence requirement in equation (6), which, with $t=\lambda l/s$, becomes $s<1p_1/(4d)$. For plane-wave case, where $p_2=p_1/2$, it is obvious from Equation (7) that this results in a maximum duty cycle of $DC=0.5$, beyond which contrast will be limited by spatial coherence.

A source array as described above can be obtained in various ways:

1) One can generate an array of electron line foci on an anode surface.

2) One can use an anode surface that is structured either topographically or that consists of regions of different materials.

3) It is also possible to generate a single line focus or spot focus that is scanned across the anode surface to produce—averaged over time—an array of lines. One advantage of such a scheme in comparison to keeping the single spot on the same place is that, due to improved heat dissipation, more power can be deposited without damaging the anode. Another advantage is that the period of the source array can be tuned via the electron beam deflection to match Eq. (7) for different values of 1/d. Moreover the beam deflection could be used to shift the source array across the anode to perform phase stepping.

Figure 11:
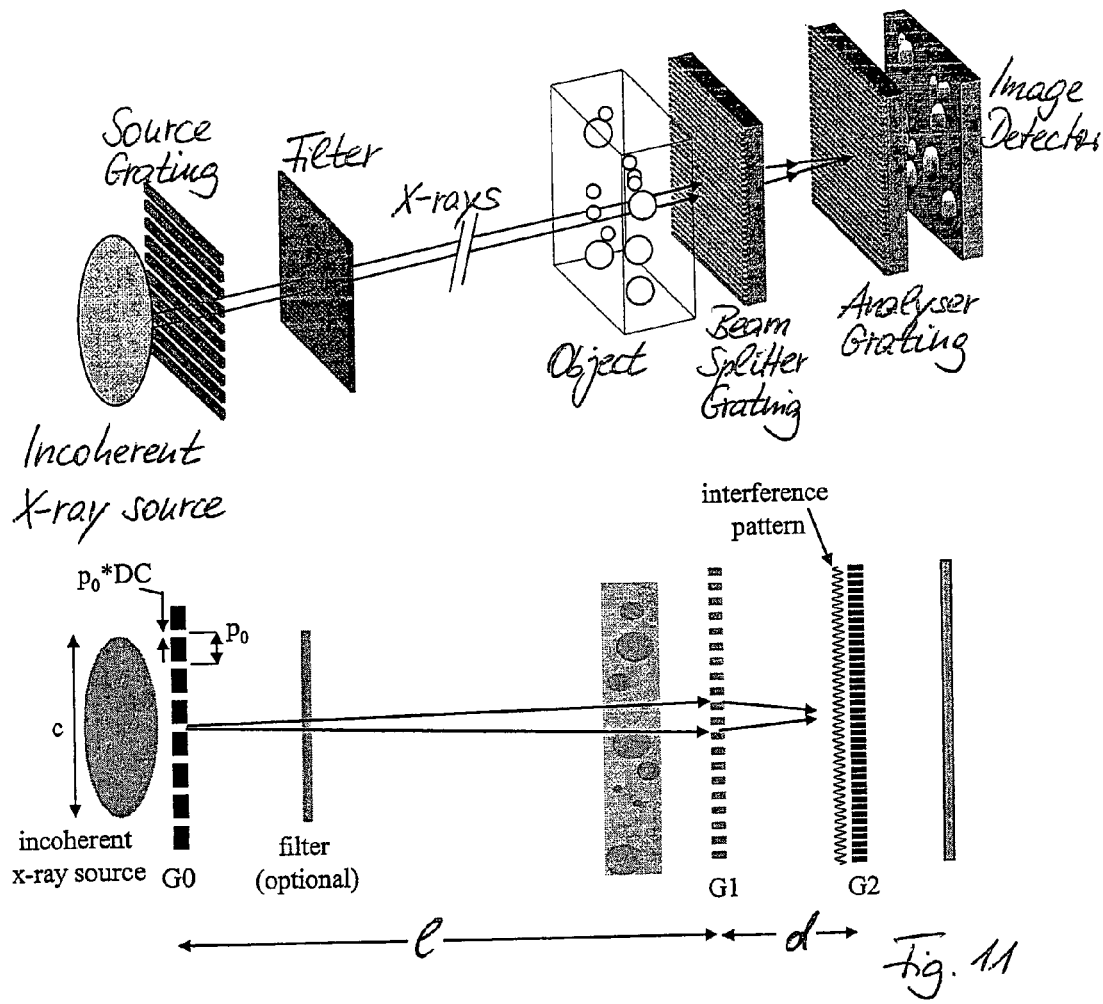
FIG. 11 a schematic view on a grating interferometer with a source grating.

4) The simplest method is to put an array of slits, i.e. an amplitude grating in front of a large x-ray source to generate an array of virtual line sources. A schematic view of such a set-up is shown in FIG. 11. Here the open fraction, or duty cycle, DC of the source grating determines the degree of spatial coherence. For smaller values of DC, the contrast of the phase images is improved at the cost of reduced flux density. As an example a typical set of parameters is calculated: For a wavelength of $\lambda=0.1$ nm, a period $p_1=4$ μm, and choosing the first fractional Talbot distance for the distance between G1 and G2 we obtain $d_n \supset p_1^2/(8\lambda)=20$ mm. For a distance l=1 m between source and beam-splitter grating G1, we obtain $p_2=2.04$ μm and $p_0=102$ μm. If the source size is 1 mm×1 mm, the slit array generates about N=10 virtual line sources, which results in a flux density 10 times higher than in a setup with a single, unstructured line source of 0.1×1 mm.

The considerations described in the previous sections in context with the two grating interferometer with a single source are also valid for the setup with an arrayed source. The possibility to perform a phase stepping scan by moving the source has to be generalized in this case: it is the entire array of sources that should be moved for phase stepping. When an array of slits is used to create the source array, then that slit-array aperture should be moved together with the source, or it may even be moved alone, with the source remaining fixed in space.

Figure 12:
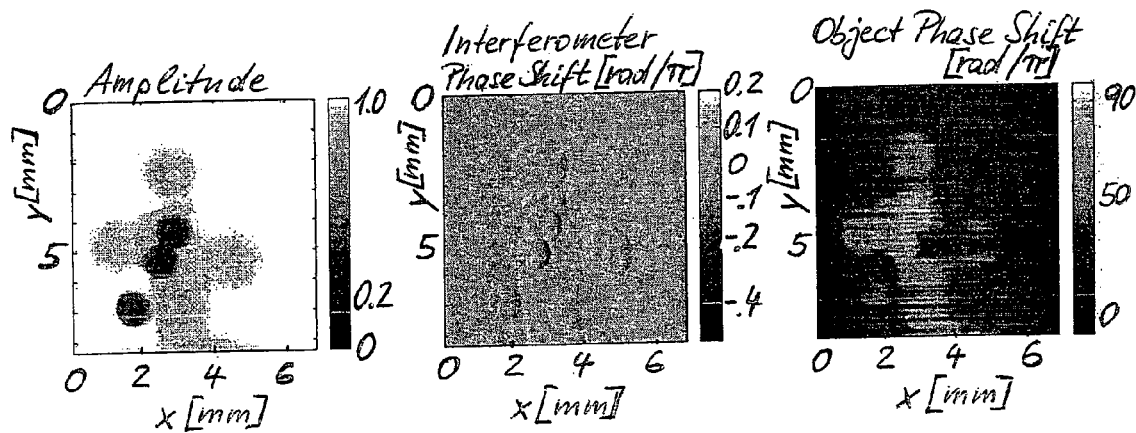
FIG. 12 X-ray images of a test sample containing aluminum and plastic spheres, recorded with polychromatic radiation from a standard laboratory x-ray source.

FIG. 12 shows images obtained under the similar conditions as those shown in FIG. 9, i.e., with a laboratory X-ray source. The important difference is that this time a source with a size of 0.8 mm×0.4 mm was used, which is far to large to provide sufficient transverse coherence for interferometric phase contrast. By mounting an additional source grating with a period of $p_0=127$ μm and a duty cycle of approximately DC=0.25, an array of virtual line sources with sufficient transverse coherence was created.

In this section, configurations particularly suited for phase contrast x-ray imaging are listed in detail. They are designed for two different applications: desktop microtomography and mammography. The latter can be implemented either with a full-field setup or a scanning setup.

A grating based interferometer for phase contrast desktop tomography system may consist of the following components:

An X-ray source of either the rotating-anode or the sealed-tube type with emission lines in the range between 5 and 10 keV. Suitable anode materials include Ti, V, Cr, Mn, Fe, Co, Ni, Cu, and Ge. In this example a design wavelength was chosen to $\lambda=0.154$ nm, which corresponds to the Cu—$K_\alpha$ emission line, at an energy of 8.0 keV. Both of the $K_\alpha$ lines (Cu $K_{\alpha 1}$ at $\lambda=0.1540$ nm, Cu $K_{\alpha 2}$ at $\lambda=0.1544$ nm) can be used simultaneously in an efficient way.

A two-dimensional digital x-ray detector, placed at a distance of 0.3–1.5 m, typically 0.8 m from the source. The number of pixels of the detector should be between 500×500 and 4000×4000, typically 2000×2000. The field of view of the detector should be between 5 and 30 mm, typically 10 mm. The pixel size of the detector is thus typically 5 μm×5 μm.

The center of the detector and the center of the source define the optical axis. The optical axis can be in any direction, but a horizontal axis is most advantageous.

A rotatable sample holder with the axis of rotation perpendicular to the optical axis is placed between the source and the detector so that a sample can be mounted with its center of gravity close to the optical axis. The distance between the sample and the source is called a, The distance between the sample and the detector is called b.

The phase grating and the absorption grating are placed directly in front of the detector. The period $p_2$ of the analyzer grating should be chosen smaller than the detector pixel size, so that the spatial resolution of the detector can be fully used. For a pixel size of 5 μm, the pitch $p_2$ should therefore be less than 3 or 4 μm, typically $p_2$=1 μm. In this case, and with λ=0.154 nm and l=0.8 m, the period of the phase grating should be $p_1$=1.992 μm (Equations 8 and 10) for operation in the first fractional Talbot distance, i.e., at an inter-grating distance d=3.23 mm (Equation 5). If silicon is used as the material for the beam-splitter grating, then a grating depth of 10.2 μm is required to obtain a phase shift of n. The intensity transmission of 10.2 μm of Si is 86.6%, so that the transmission of an Si grating with that thickness and a duty cycle of 0.5 would be 93.3%. If poly-methyl-methacrylate (PMMA) is used as the material for the beam-splitter grating, then the ideal grating depth is 18.7 μm. The intensity transmission of such a grating would be 99.3% (for a duty cycle of 0.5). The use of other polymers would result in similar figures. For the absorption grating, if gold is used as the material, a thickness of 6 μm would ensure an absorption of more than 90%, and 12 μm thickness would result in more than 99% of absorption in the grating lines.

An arrayed source, technically realized, e.g., by slit-array aperture. In this case, the slit-array period should be $p_0$=0.248 mm (obtained from Equation 10), max. size of array (in direction perpendicular to slits) c=1.24 mm, given by the condition that penumbral blurring should not exceed the pixel size, max. gap size of each slit 0.124 mm (i.e., DC=0.5), given by coherence requirement.

A grating based interferometer for a phase contrast full-field digital mammography (FFDM) system could consist of the following components:

An x-ray source of either the rotating anode or a sealed tube type with an anode with emission lines in the 15-25 keV region. Anode materials could be Nb, Mo, Rh, Pd, or Ag. In this example we choose a design wavelength λ=0.056 nm corresponding to the Ag—$K_<$ emission at 22 keV energy (Ag $K_{\alpha 1}$ at λ=0.0559 nm, Ag $K_{\alpha 2}$ at λ=0.0564 nm). The design of the entire apparatus can be based on that of common (absorption-contrast) FFDM systems, with the source array, beam splitter and analyzer as new, different elements.

A filter of Pd or Rh or another material with an x-ray absorption edge in the 23-30 keV energy range and a thickness between 20 and 100 μm, typically 50 μm may be used to suppress unwanted parts of the spectrum.

A gantry with compression paddle as commonly used in mammography screening systems comprises a two-dimensional digital flat-panel x-ray detector, placed at a distance of 0.5-1.0 m from the source, just below (i.e., downstream of) the gantry. Here 1.0 m as the distance was used. The field of view of the detector should be not much smaller than $(200\ mm)^2$, preferably around 240× 300 $mm^2$. (i.e., the size of the largest commonly used film cassette in conventional mammography). The pixel size of the detector is typically between 50 and 100 μm in each dimension, so that the detector has between $(2500)^2$ and $(5000)^2$ pixels. (These are the characteristics of most commercially available detectors for FFDM.) Here, a pixel size of 70 μm is assumed.

A suitable set of parameters for the grating periods, source array dimensions, and distances is $p_2$=3 μm (period of the analyzer grating), $p_1$=8.4 μm (period of the phase grating), $p_0$=26.6 μm (spacing of the virtual line sources). With a distance l=1.0 m between the source array and the phase grating, the first fractional Talbot distance is $d_1$=74.8 mm. The total size of the source array should, with these parameters, not exceed 0.4 mm, i.e., the maximum number of virtual line sources is 15. For the phase grating, if nickel is used as the material, the thickness required to achieve a phase shift of n is 7.7 μm, resulting in an average intensity transmission of 92.6% (for a duty cycle of 0.5). The analyzer grating, if made of gold, should have a minimum thickness of 20 μm, which yields absorption of 90% in the grating lines.

In a slot-scanning mammography setup (possibly based on existing non-interferometric slot-scanning systems), the source material, distances and grating periods can be chosen similar or identical to the FFDM example above. The following items would be different or additional with respect to the FFDM setup:

A first collimator (one slit or a sequence of slits), made of a strongly absorbing material, should be mounted between the source and the object position. Together with the spots of an arrayed virtual source, this collimator defines a fan-shaped beam.

A second collimator slit, made of a strongly absorbing material, should be mounted just above (i.e., upstream of) the interferometer gratings.

The detector can be a line-array detector, for example a direct-detection detector. The detector elements should have non-square shape, with a size between 25 and 100 μm (corresponding to the desired resolution) along the line of detector elements and several millimeters (corresponding to the width of the collimator slits) in the other dimension.

The collimator slits, the interferometer gratings and the detector should be parallel to each other. The lines of the interferometer gratings should be parallel to the fan-opening plane.

The collimators and the detector can be rotated around the source array, perpendicular to the fan-opening plane, over an angular range large enough to cover one dimension of the field of view mentioned in the FFDM setup. For the acquisition of a mammogram, these components will be scanned together.

All of the considerations above can be applied to an interferometer that resembles the one presented, with the only difference that the beam-splitter grating G1 is not a phase grating, but an absorption grating, i.e., its lines strongly absorb X rays. The use of an absorption grating as the beam splitter is less advantageous than that of a phase grating because even a perfect absorption grating (completely opaque lines, duty cycle exactly 0.5) will only deliver 20% of the incoming intensity into the negative and positive first orders. 50% of the incident power are absorbed in the grating, and one-half of the remaining 50% go into the zeroth order, or undiffracted portion of the beam, contributing to background signal and/or radiation dose deposited in the object or patient. A phase grating is four times more efficient. Nonetheless, for a number of applications where these drawbacks can be tolerated and/or where a phase grating is not available, the use of an absorption grating as beam splitter can make sense.

In this case, all of the considerations for interferometer design laid out above remain valid with the following modifications:

The relation between the periods of G1 and G2 is different. Equation 1 (section 3.1) becomes $$p_2 = p_1 \cdot \frac{(d+l)}{l} \tag{1'}$$

The Talbot distances at which the contrast is best (section 3.6) are $d_n = n\, p_1^2/\lambda$ for a plane illuminating wave and $$d'_{n,sph.} = \frac{l \cdot d'_n}{l - d'_n} = \frac{l \cdot n \cdot p_1^2/\lambda}{l - n \cdot p_1^2/\lambda} \tag{5'}$$

for a spherical wave, which replaces Equation (5).

The relationship between $p_0$, $p_1$, and $p_2$ (Equation 8) changes to $$p_1 = \frac{p_0 p_2}{p_0 + p_2} .. \tag{8'}$$

The invention claimed is:

1. An interferometer for X-rays, in particular hard X-rays, for obtaining quantitative phase contrast images, comprising:
   a) a standard polychromatic X-ray source,
   b) a diffractive optical beam splitter other than a Bragg crystal in transmission geometry, and
   c) a position-sensitive detector with spatially modulated detection sensitivity.

2. The interferometer according to claim 1, wherein the beam splitter is one of a line grating and a two-dimensionally structured grating.

3. The interferometer according to claim 1, wherein the beam splitter is a phase grating made by deep etching into silicon or a polymer and having an X-ray phase shift of n or odd multiples thereof.

4. The interferometer according to claim 2, wherein an analyzer grating is disposed between the beam splitter and the position-sensitive detector, wherein the analyzer grating has a one- or two-dimensional grating structure with high X-ray absorption contrast, and is placed in front of the detector.

5. The interferometer according to claim 4, wherein the analyzer grating is made by deposition of a heavy metal into gaps of a low-absorbing structure.

6. The interferometer according to claim 5, wherein a period of the analyzer grating and a period of the grating of the beam splitter are matched to a radius of curvature of an incident wavefront by a relation $$p_2 = \frac{1}{2} p_1 \cdot \frac{(d+l)}{l},$$

where p1 is the period of the beam splitter; p2 is the period of the analyzer grating;
d is a distance between the beam splitter and the analyzer grating; and
l is a distance between the X-ray source and the beam splitter.

7. The interferometer according to claim 6, wherein a distance between the grating of the beam splitter and the analyzer grating is chosen to be an odd fractional Talbot distance, given by the equation $$d_{n,sph.} = \frac{l \cdot d_n}{l - d_n} = \frac{l \cdot n \cdot p_1^2/(8\lambda)}{l - n \cdot p_1^2/(8\lambda)},$$

where n=1, 3, 5, . . . .

8. The interferometer according to claim 7, wherein a phase shift of the grating of the beam splitter and the distance between the beam splitter and the analyzer grating are adapted to a photon energy corresponding to an emission line of the X-ray source.

9. The interferometer according to claim 5, wherein a mechanism is comprised to vary an angular orientation around an optical axis of the beam splitter with respect to the analyzer to provide for one of:
   observing moiré fringes of a desired period,
   minimizing moiré fringes, and
   suppressing moiré fringes.

10. The interferometer according to claim 4, wherein a mechanism is comprised to place a sample to be investigated between the X-ray source and the beam splitter or between the beam splitter and the analyzer grating.

11. An interferometer according to claim 4, wherein the detector is position-sensitive in two dimensions, and lateral dimensions of the beam splitter and the analyzer grating cover a significant portion of an active area of the detector.

12. The interferometer according to claim 10, wherein a collimator placed between the X-ray source and the beam splitter limits a spatial extent of illuminating X rays to a fan beam, wherein the detector is a line-array detector, and wherein a mechanism is comprised that allows a linear scan of the sample relative to the interferometer, perpendicular to an opening angle of the fan beam.

13. The interferometer according to claim 1 wherein the X-ray source comprises a one- or two-dimensional array of individual sources whose lateral separation p0 is given by $$p_0 = p_2 \times \frac{l}{d}.$$

or integer multiples thereof.

14. The interferometer according to claim 13, wherein the array of sources is generated by an aperture mask with line- or dot-shaped openings.

15. The interferometer according to claim 13, wherein the array of sources is generated by electron optics that creates an array of electron line or dot foci on an anode of the X-ray source.

16. The interferometer according to claim 13, wherein the array of sources is generated by electron optics that scans a single line or dot focus across an anode surface of the X-ray source.

17. The interferometer according to claim 13, wherein the array of sources is generated by using an X-ray source comprising an anode which is structured either topographically or assembled in a mosaic manner from different materials.

18. The interferometer according to claim 10, comprising means for rotating the sample relatively to remaining components of the interferometer in order to perform data collection for a tomography scan.

19. The interferometer according to claim 1, wherein an analysis procedure is implemented for data provided by a phase-stepping scan that comprises the steps of calculating, for each element of the detector, the Fourier transform or at least one Fourier component of an intensity curve measured in the element, and then retaining a phase of one or more Fourier components as a signal for further processing.

20. The interferometer according to claims 1, wherein an analysis procedure is implemented for data provided by a phase-stepping scan that comprises the steps of fitting, for each element of the detector, an intensity curve measured in the element to an intensity curve modeled or measured separately without beam distortions under study, where at least one of fit parameters is the shift of the curve along the position axis of the scan.

21. The interferometer according to claim 1, wherein the beamsplitter is an absorption grating.

22. The interferometer according to claim 1, further including a mechanism configured to perform a one- or two-dimensional phase stepping scan by tilting the interferometer with respect to the X-ray source.

23. An interferometer for X-rays, in particular hard X-rays, for obtaining quantitative phase contrast images, comprising:
   a) a standard polychromatic X-ray source,
   b) a diffractive optical beam splitter other than a Bragg crystal in transmission geometry,
   c) a position-sensitive detector with spatially modulated detection sensitivity; and
   d) a mechanism configured to perform a one- or two-dimensional phase stepping scan by lateral transverse movement of one of the X-ray source, an aperture located in front of the X-ray source, the beam splitter, and the analyzer grating.

* * * * *